United States Patent
Dean et al.

(10) Patent No.: US 9,610,443 B1
(45) Date of Patent: Apr. 4, 2017

(54) METHODS TO TRIGGER HIGH AMPLITUDE OSCILLATIONS OR RESONANCE IN THE CARDIOVASCULAR SYSTEM OF A PATIENT USING ELECTRICAL STIMULATION

(71) Applicants: Steven G Dean, New York, NY (US);
Frederick Muench, Brooklyn, NY (US)

(72) Inventors: Steven G Dean, New York, NY (US);
Frederick Muench, Brooklyn, NY (US)

( * ) Notice: Subject to any disclaimer, the term of this patent is extended or adjusted under 35 U.S.C. 154(b) by 0 days.

(21) Appl. No.: 14/608,109

(22) Filed: Jan. 28, 2015

Related U.S. Application Data

(63) Continuation-in-part of application No. 13/779,613, filed on Feb. 27, 2013, and a continuation-in-part of application No. 14/198,312, filed on Mar. 5, 2014.

(60) Provisional application No. 61/933,250, filed on Jan. 29, 2014, provisional application No. 61/933,255, filed on Jan. 29, 2014.

(51) Int. Cl.
*A61N 1/36* (2006.01)

(52) U.S. Cl.
CPC ..... *A61N 1/36014* (2013.01); *A61N 1/36025* (2013.01)

(58) Field of Classification Search
CPC ................. A61N 1/36014; A61N 1/36025
See application file for complete search history.

(56) References Cited

U.S. PATENT DOCUMENTS

| | | | |
|---|---|---|---|
| 4,315,502 A | 2/1982 | Gorges | |
| 6,299,632 B1 | 10/2001 | Jaillet | |
| 6,662,032 B1 | 12/2003 | Gavish et al. | |
| 7,311,658 B2 | 12/2007 | Elliot | |
| 7,643,875 B2 | 1/2010 | Heil et al. | |
| 8,219,188 B2 | 7/2012 | Graig | |
| 8,442,632 B2 | 5/2013 | Kullock et al. | |
| 2010/0249860 A1* | 9/2010 | Shuros | A61N 1/3625 607/4 |

FOREIGN PATENT DOCUMENTS

| | | |
|---|---|---|
| WO | WO 2008/131553 | 4/2007 |
| WO | WO 2010/047834 | 10/2008 |
| WO | WO 2014/170880 | 4/2014 |

OTHER PUBLICATIONS

U.S. Appl. No. 13/779,613, filed Feb. 27, 2013, Muench, et al.
U.S. Appl. No. 14/198,312, filed Mar. 5, 2014, Muench, et al.

(Continued)

*Primary Examiner* — Rex R Holmes
(74) *Attorney, Agent, or Firm* — Byrne Poh LLP

(57) ABSTRACT

Various embodiments of and methods for providing external therapeutic electrical stimulation to a patient are disclosed and described. Therapeutic external electrical stimulation is provided to at least one location on a patient's skin, or through clothing or a layer disposed next to the patient's skin, and is configured to trigger or induce resonance or high amplitude oscillations in a cardiovascular system of the patient. Inducing such resonance can aid in training autonomic reflexes and improve their functioning.

17 Claims, 5 Drawing Sheets

(56) References Cited

OTHER PUBLICATIONS

Doucet, B.M., et al., Neuromuscular Electrical Stimulation for Skeletal Muscle Function, Yale Jrnl. of Biology and Medicine 85 (2012), pp. 201-215.
Alpha-Stim Aid and You, brochure c. 2014 by Electromedical Products Int'l Inc.
Grote, V., et al., Cardio-autonomic Control and Wellbeing Due to Oscillating Color Light Exposure, Physiology & Behavior 114-115 (2013) 55-64.
Hashmi, J.T., et al., Effect of Pulsing in Low-Level Light Therapy, Lasers Surg Med. Aug. 2010; 42(6): 450-466.

\* cited by examiner

METHODS TO TRIGGER HIGH AMPLITUDE OSCILLATIONS OR RESONANCE IN THE CARDIOVASCULAR SYSTEM OF A PATIENT USING ELECTRICAL STIMULATION

RELATED APPLICATIONS

This application claims priority and other benefits from: (a) U.S. Provisional Patent Application Ser. No. 61/933,250 entitled "Electrical Stimulation to Trigger High Amplitude Oscillations or Resonance in the Cardiovascular System of a Patient" to Dean et al. filed on Jan. 29, 2014 (hereafter "the '250 patent application"), and (b) U.S. Provisional Patent Application Ser. No. 61/933,255 entitled "Manipulating Electromagnetic Radiation to Trigger High Amplitude Oscillations or Resonance in the Cardiovascular System" to Dean et al. filed on Jan. 29, 2014 (hereafter "the '255 patent application").

This application also claims priority and other benefits from, and is a continuation-in-part of each of: (c) co-pending U.S. Utility patent application Ser. No. 13/779,613 entitled "Systems, Devices, Components and Methods for Triggering or Inducing Resonance or High Amplitude Oscillations in a Cardiovascular System of a Patient" to Muench et al. filed on Feb. 27, 2013 (hereafter "the '613 patent application), and (d) co-pending U.S. Utility patent application Ser. No. 14/198,312 entitled "Systems, Devices, Components and Methods for Triggering or Inducing Resonance or High Amplitude Oscillations in a Cardiovascular System of a Patient" to Muench et al. filed on Mar. 5, 2014 (hereafter "the '312 patent application").

Each of the foregoing four patent applications, namely the '250 patent application, the '255 patent application, the '613 patent application, and the '312 patent application, is hereby incorporated by reference herein, each in its respective entirety.

FIELD OF THE INVENTION

Various embodiments of the invention described herein relate to the field of methods, systems, devices and components for delivering external electrical stimulation therapy to a patient to induce or trigger high amplitude oscillations or resonance in the cardiovascular system of a patient.

BACKGROUND

Low or reduced baroreflex sensitivity in patients is associated with numerous problems and disorders (e.g., hypertension, congestive heart failure, coronary heart disease, hypertension, depression, alcohol or drug use disorders and aging). Reduced baroreflex sensitivity in patients blunts the flexibility of the body's self-regulatory system. Contrariwise, high baroreflex sensitivity in patients is generally associated with health and wellness.

What is needed, therefore, are efficacious and cost effective means and methods for increasing baroreflex sensitivity in patients.

Various printed publications, patents and patent applications containing subject matter relating directly or indirectly to the methods, systems, devices and components described below include, but are not limited to, the following:

Vaschillo, E. G., Vaschillo, B., Lehrer, P. M. Characteristics of Resonance in Heart Rate Variability Stimulated by Biofeedback. Applied Psychophysiology and Biofeedback. 2006, June; 31(2): 129-142.

Vaschillo, E G, Vaschillo, B, Buckman, J F, Pandina, R J, and Bates, M E. The Investigation and Clinical Significance of Resonance in the Heart Rate and Vascular Tone Baroreflexes. In BIOSTEC 2010, CCIS 127, A. Fred, J. Filipe, and H. Gamboa (Eds.), pp. 224-237, Springer, Heidelberg.

Vaschillo, E. G., Bates, M, Vaschillo, B., Lehrer, P. M., et al. Heart rate variability response to alcohol, placebo, and emotional picture cue challenges: Effects of 0.1-Hz stimulation, *Psychophysiology,* 45 (2008), 847-858.

France C R, France J L, Patterson S M. Blood pressure and cerebral oxygenation responses to skeletal muscle tension: a comparison of two physical maneuvers to prevent vasovagal reactions. Clinical Physiology and Functional Imaging. 2006; 26:21-25.

Vaschillo, E. G., Bates, M. E., Vaschillo, B., Lehrer, P., Udo, Lehrer P, Vaschillo E, Trost Z, France C. Effects of rhythmical muscle tension at 0.1 Hz on cardiovascular resonance and the baroreflex. Biological Psychology. 2009; 81:24-30.

Wheat, A. & Larkin, K. Biofeedback of Heart Rate Variability and Related Physiology: A Critical Review Applied Psychophysiology and Biofeedback. 2010, 35: 3: 229-242.

Vaschillo, E. G., Vaschillo, B., Pandina, R. J. and Bates, M. E. (2011), Resonances in the cardiovascular system caused by rhythmical muscle tension. Psychophysiology, 48: 927-936.

Doucet, B. M., Lam, A., & Griffin, L. (2012). Neuromuscular Electrical Stimulation for Skeletal Muscle Function. *The Yale Journal of Biology and Medicine,* 85(2), 201-215.

Alphastim product manual, http://www.alpha-stim.com/wp-content/uploads/brochures/AlphaStim AID Patient Brochure.pdf, Nov. 11, 2014.

U.S. Pat. No. 8,442,632 to Kullock et al. for "Method and apparatus for affecting the autonomic nervous system," Oct. 21, 1998.

U.S. Pat. No. 6,662,032 to Gavish et al. for "Interventive-diagnostic device," Jul. 6, 1999.

U.S. Pat. No. 5,997,482 to Vaschillo et al. for "Therapeutic method for a human subject," Dec. 7, 1999.

U.S. Pat. No. 7,643,875 to Heil et al. for "Baroreflex stimulation system to reduce hypertension," Dec. 23, 2003.

U.S. Pat. No. 8,219,188 to Graig for "Synchronization of vagus nerve stimulation with the cardiac cycle of a patient," Mar. 29, 2006.

U.S. Pat. No. 7,117,032 to Childre et al. for "Systems and methods for facilitating physiological coherence using respiration training," Oct. 3, 2006.

WO patent No. 2010047834 to Kirsch et al. entitled "Microcurrent and cranial electrotherapy stimulator for control of anxiety, insomnia depression and pain," Oct. 23, 2008.

U.S. patent application Ser. No. 13/779,613 to Muench et al. for "Systems, Devices, Components and Methods using Vibration to Trigger High Amplitude Oscillations or Resonance in the Cardiovascular System of a Patient," Feb. 28, 2012.

U.S. patent application Ser. No. 14/198,312 to Muench et al. entitled "Systems, Devices, Components and Methods for Triggering or Inducing Resonance or High Amplitude Oscillations in a Cardiovascular System of a Patient," Mar. 5, 2014.

U.S. Patent Publication No. 2012/0277521 to Chamberlain for "Systems and methods for eliciting a therapeutic zone," Nov. 1, 2012.

The dates of the foregoing publications may correspond to any one of priority dates, filing dates, publication dates, issue dates and retrieval dates. Listing of the above patents and patent applications in this background section is not, and shall not be construed as, an admission by the applicants or their counsel that one or more publications from the above list constitutes prior art in respect of the applicant's various inventions. All printed publications and patents referenced herein are hereby incorporated by referenced herein, each in its respective entirety.

Upon having read and understood the Summary, Detailed Descriptions and Claims set forth below, those skilled in the art will appreciate that at least some of the methods, systems, devices and components disclosed in the printed publications listed herein may be modified advantageously in accordance with the teachings of the various embodiments that are disclosed and described herein.

SUMMARY

Resonance or high amplitude oscillations can be induced or created in the cardiovascular system (CVS) by providing electrical stimulation therapy at specific frequencies either close to or according to a patient's resonant frequency.

In one embodiment, there is provided a method of providing external electrical stimulation therapy to a patient, comprising: delivering at least one electrical stimulation signal to at least one location on the patient's skin, or through clothing or a layer disposed next to the patient's skin, the electrical stimulation signal being successively delivered to the patient over first periods of time and not being delivered to the patient over second periods of time, the second period of time being interposed between the first periods of time; wherein the first and second periods of time are together configured to create third periods of time which are configured to trigger or induce resonance or high amplitude oscillations in a cardiovascular system of the patient.

Further embodiments will become apparent to those skilled in the art after having read and understood the specification and drawings hereof.

BRIEF DESCRIPTION OF THE DRAWINGS

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Figure 1:
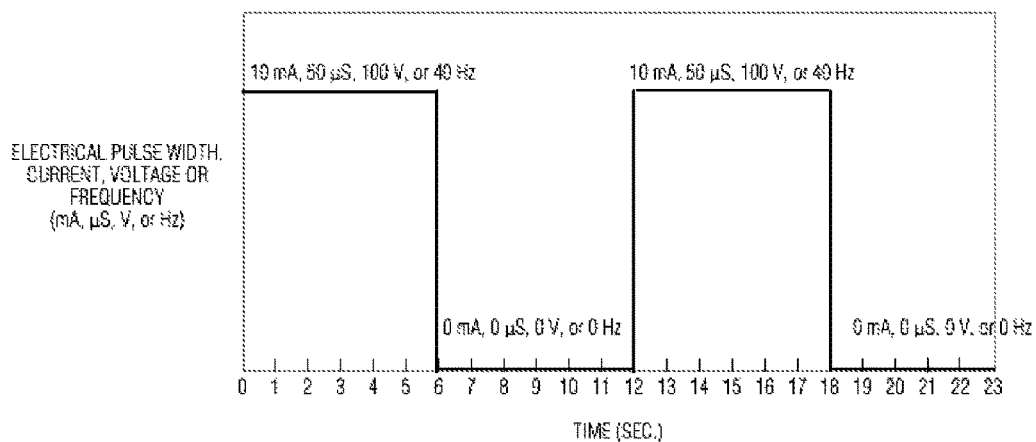
FIGS. 1 through 3 illustrate various embodiments of external electrical stimulation regimes and corresponding methods that can be provided to a patient.

Described herein are various embodiments of external electrical stimulation methods that are configured to trigger or induce resonance or high amplitude oscillations in a cardiovascular system of the patient.

Disclosed and described herein are various methods, systems, devices and components for entraining frequencies in the CVS using external noninvasive electrical stimulation devices and techniques.

The arterial baroreflex system (BRS) is a reflexive control system that counteracts acute shifts in blood pressure (BP) by invoking compensatory reactions in cardiovascular functions (e.g., heart rate (HR), vascular tone (VT), and stroke volume (SV). Baroreceptors trigger simultaneous reflexive reactions in HR, VT, and SV. The BRS regulates short-term BP serving to protect the brain from stroke and the heart from myocardial infarction as well as to restore its inhibition-excitation balance. Low or reduced baroreflex sensitivity is often associated with numerous problems and disorders, such as hypertension, congestive heart failure, coronary heart disease, depression and aging. Reduced baroreflex sensitivity blunts the flexibility of the regulatory system, whereas a high sensitivity is associated with health and wellness.

Similar to engineering closed loop control systems with delays, the closed loop baroreflex system has been discovered to possess resonance properties. That is, there are certain frequencies (known as resonant or resonance frequencies) at which stimulation of the baroreflex system can elicit high amplitude oscillations in HR, BP, SV, and/or VT. The value of the delay in the feedback control system can be used to define one or more resonant frequencies in the closed loop control system. In one such embodiment, the period of the resonant oscillations is equal to the value of two delays. In a closed loop baroreflex system, periodic driving forces at one or more resonant frequencies can produce much larger amplitudes. This is because a baroreflex system is characterized by delays between changes in BP and HR (~5 seconds), (i.e., periods of resonance oscillation are ~10 s). Each person's baroreflex system has own delays and accordingly own resonance frequencies. These changes can coincide in some fashion with, or can be proportional to, certain resonant frequencies.

Interventions such as slow meditative breathing and progressive muscle relaxation performed at or near a patient's resonant frequency can increase oscillations at these frequencies and increase short-term HR baroreflex sensitivity, vagal tone, and/or heart rate variability. This is especially so in healthy individuals and in patients who suffer from cardiovascular or autonomic nervous system disorders. Like many systems, the cardiovascular system has many different functions, and is characterized by several distinct resonant frequencies.

The baroreflex system in humans can demonstrate resonance properties at frequencies of about 0.1 Hz. In an HR baroreflex closed-loop system, a shift in BP can cause a compensatory HR response that is delayed for approximately 5 seconds. These delays of approximately 5 seconds can in turn coincide with resonance oscillations of about 0.1 Hz (since oscillation periods are equal to twice the value of the delay—e.g., a cycle of about 10 seconds comprised of adjacent 5 second periods). One mechanism to create or induce resonance in an HR baroreflex system is through slow paced breathing at an average of about 6 full cycles per minute in which an individual inhales for approximately 4-7 seconds and exhales for approximately 4-7 seconds. Doing so results in individual inhalation-exhalation cycles of about 8-14 seconds. While rates vary according to the individual, breathing at such rates can produce high amplitude oscillations in the HR baroflex system that typically range between about 0.075 Hz and about 0.125 Hz, depending on short-term baroreflex sensitivity and short-term heart rate variability. Long-term practice of such breathing patterns has been linked to an increase in baroreflex sensitivity and HRV at rest. It is therefore possible to cause or induce resonance in the CVS through manipulation of breathing, auditory and visual stimuli, or rhythmical muscle relaxation.

Research directed specifically to the effects of breathing at approximately the foregoing rates has revealed potential effects on the CVS, with potential cascading effects on disorders associated with vagal and autonomic dysfunction. Some studies have revealed that paced breathing at a rate of approximately 0.1 Hz can be used effectively in heart rate variability (HRV) biofeedback techniques, as described for example by Lehrer and Vaschillo (2003). Some studies have also revealed that entraining the CVS and breathing at about 0.1 Hz can improve the symptoms of numerous disorders, such as depression, PTSD, fibromyalgia, hypertension, abdominal pain, and coronary heart disease (Vaschillo et al., 2010; Wheat and Larkin, 2010). As noted by Vaschillo and colleagues in 2010, "the therapeutic effects of HRV biofeedback are thought to be due to the induction of high-amplitude oscillations in HR, BP, and VT at specific frequencies which exercise and activate homeostatic reflexes (e.g., the baroreflex reflex), retrain them, and initiate, through the baroreceptors, a cascade of neurobiological events that produces a generalized inhibitory effect on the brain."

Other methods to cause high-amplitude oscillation in HR, BP, and VT at specific frequencies may exist, including presenting emotional pictures at a ten second cycle (5 seconds with pictures, 5 seconds without pictures—see Vaschillo et al., 2010), and self-induced rhythmical muscle tension stimulation at the same frequency (France et al., 2006; Lehrer et al., 2009). External or patient-induced stimulation provided at specific frequencies thus may entrain similar frequencies in the CVS through increasing spectral power in the inter-beat interval (RRI), blood pressure (BP) and pulse transit time (PTT). External or patient-induced stimulation may also improve other areas of functioning such as increases in cerebral oxygenation (see, e.g., France, France, & Patterson, 2006). External stimulation through visual pictures or muscle tension exercises might also produce similar clinical effects in the CVS as those produced by breathing biofeedback techniques. Treating diseases associated with cardiovascular dysfunction using external stimulation techniques or patient-induced stimulation, such as hypertension, atrial fibrillation, mental health disorders, depression, post-traumatic stress disorder and substance abuse, may also be possible.

The average stimulation frequency of the HR-baroreflex system is approximately 0.1 Hz (or 6 cycles per minute). When referring to resonance frequency herein, we generally mean the resonance frequency of the HR baroreflex system and the HR component of the CVS. Individual differences in the optimal frequency to create resonance in the CVS exist, however, and can range between 4 and 7 cycles per minute. These differences are called individual resonance frequencies, specifically HR resonance frequencies and can be calculated using analysis of heart rate variability patterns. These differences have been noted to be associated with differences in blood volume, and can be roughly estimated using height and gender information. Taller individuals and males have longer stimulation rates (e.g. taller individuals have longer total cycles) to create HR resonance.

In addition to creating increased oscillations at the above resonance frequencies which increase dramatically when stimulated, CVS functions may be entrained at other frequencies through breathing at higher or lower rates. Frequencies entrained in the CVS correspond roughly to a total period of one cycle of inhalation and exhalation combined, indicating that the CVS might be entrained using a range of active and/or inactive stimulation cycles. As described above, then, breathing and external stimulation through visual pictures or muscle tension exercises can produce changes in the CVS exhibited through high amplitude oscillations at frequencies that approximately mirror the frequency of breathing, for example.

External stimulation via manipulations of electrical stimulation in various forms can also entrain the CVS to increase oscillations at specific CVS frequencies and create CVS resonance. This can have profound implications for the treatment of numerous psychiatric and medical disorders, particularly depression and cardiovascular disease, which are often associated with dysregulation in the cardiovascular system. As indicated in our previous application using vibration (U.S. patent application Ser. No. 13/779,613), these methods can induce resonance or high amplitude oscillations passively rather than requiring active involvement from the patient (e.g., paced breathing or muscle tension). The high amplitude oscillation of cardiovascular functions at resonant frequencies generated by such stimulation can help regulate the CVS, modulate the vagus nerve and the brain, and normalize the inhibition-excitation balance of the CVS on brain systems, and in such a manner provide beneficial therapy to a patient. In some embodiments, the electrical stimulation cycle can entrain the CVS at a frequency or period that mirrors a combined on-off cycle or increasing-decreasing frequency provided by the methods, systems, devices and components described and disclosed herein.

To our knowledge, and other than the various embodiments described and disclosed herein, there are no known electrical stimulation methods that include our on-off or increasing-decreasing periods to induce resonance or high amplitude oscillations in the CVS of a patient. However, the inclusion of these methods in combination with standard electrical stimulation methods for the general population could provide a powerful mechanism to improve outcomes beyond what is currently being done as well as offer a new method for improving mental and physical health and wellness.

In U.S. Pat. No. 6,662,032, Gavish et al. describe methods that use a range of triggers, breathing sensors and music to trigger voluntary therapeutic breathing at specific frequencies and other voluntary actions. Using cues, they alert the user to voluntarily follow these cues to change aspects of their physiology. In contrast, some of the embodiments described herein employ one or more resonance frequencies to create a cycle, by creating specific cycles and two specific periods within those cycles, that are delivered without any voluntary effort by the user. Such embodiments are completely passive to the user and the therapeutic effects involve no voluntary effort, similar to the therapy provided by a pacemaker or implantable automated vagus nerve stimulator External stimulation via manipulations of electrical stimulation in various forms can also entrain the CVS to increase oscillations at specific CVS frequencies and create CVS resonance without any voluntary action by the user aside from turning a device on and off. This can have profound implications for the treatment of numerous psychiatric and medical disorders, particularly depression and cardiovascular disease, which are often associated with dysregulation in the cardiovascular system and decreased vagal tone. Previous methods to induce resonance or high amplitude oscillations often required active involvement from the patient (e.g., paced breathing or muscle tension). Various embodiments described herein provide passive means to stimulate reflexes, which can extend therapeutic effects to a significantly larger patient population.

Resonance or high amplitude oscillations can be induced or created in the CVS by means of a system or device that creates and/or delivers external electrical stimulation according to a external electrical stimulation therapy stimulation regime, which according to some embodiments is predetermined (e.g., by one's resonance frequency or pre-programmed). Examples of such external electrical stimulation regimes for the HR baroreflex system include an 8-14 second cycle (e.g., on for about 4-7 seconds and off for about 4-7 seconds, or increasing in external electrical stimulation frequency for about 4-7 seconds and decreasing in external electrical stimulation frequency for about 4-7 seconds). This can be more specifically achieved by finding an individual patient's resonance frequency in specific ranges between about 0.075 Hz and about 0.125 Hz. However, there is evidence that one can entrain the CVS at nearly any frequency within the human range to increase specific oscillations in the CVS.

Disclosed and described herein are techniques for entraining frequencies in the CVS using any form of external or noninvasive electrical stimulation wherein external or noninvasive refers to any form of external electrical stimulation, such as, by way of non-limiting example, on the skin, body, or garment of an individual, or that does not require invasive surgery. In general, external electrical stimulation is usually done using a range of special devices that include a low voltage current generator and electrodes through which such current comes into contact with a part of body. Various parameters of the electrical stimulation provided by such a device can be varied, such as the amplitude, amount or intensity of the current and/or voltage delivered the stimulation signal, and/or the stimulation signal's pulse width, frequency and/or duration. The greater the amplitude or magnitude of the stimulation, typically the greater the intensity (A, mA, V or mV). The larger the pulse width (sec. or μS) of the electrical pulse, typically the more aggressive the stimulation. The greater the frequency (Hz) of the stimulation, the more pulses per unit of time. The electrical stimulation described herein can include manipulation or modulation of one or more of the pulse width (μS), amplitude (mA), or frequency (Hz) to induce resonance or high amplitude oscillations in the CVS. Various embodiments automatize and employ specific cycles of on-off or increasing-decreasing electrical stimulation to entrain the CVS. Electrical stimulation can be delivered in any form of external or noninvasive electrical stimulation products or devices, including, but not limited to, devices that deliver or produce transcutaneous electrical nerve stimulation (TENS), transcranial electrical stimulation, and electrical muscle stimulation. However, other forms of stimulation using electrical currents to manipulate therapeutic tools such as electromagnetic therapy (or the manipulation of electromagnetic radiation) or pulsed electromagnetic fields (PEMF) may also be employed in accordance with the various embodiments disclosed herein.

Some embodiments induce resonance or high amplitude oscillations in the CVS of a person using specific on-off and/or increasing-decreasing periods of electrical stimulation provided over a distinct or predetermined period of time. Resonance or high amplitude oscillations can be induced or created in the CVS by means of a method system, device, or component that is configured to create and/or deliver any form of suitable electrical stimulation to a patient, where the stimulation signal is successively delivered to the patient over first periods of time (or increasing over the first period of time) and not being delivered to the patient over second periods of time (or decreasing over the second period of time), the second periods of time being interposed between the first periods of time, where the at least one stimulation signal and the first and second periods of time are together configured to trigger a third period or total cycle designed to induce resonance or high amplitude oscillations in a cardiovascular system of the patient. The third period can be determined by finding one's resonance frequency and beginning the cycle. The third period of time can also be employed to estimate an individual patient's resonance frequency, and to then induce or increase oscillations at that frequency via appropriately modulated or modified electrical stimulation. In one embodiment, the third period created by the interposed first and second periods can range between about 8 and about 14 seconds. In one embodiment, the first period can range between about 4 seconds and about 7 seconds, and the second period of time can range between about 4 seconds and about 7, seconds creating a total cycle or third period of between about 8 seconds and about 14 seconds.

In some embodiments, the stimulation cycles described above are implemented using different forms of electrical stimulation in which the cycles or third periods are repeated consecutively to induce resonance or high amplitude oscillations in the cardiovascular system of a patient for periods of time that are determined by a patient, according to programming of the device delivering the stimulation, or according to parameters programmed or specified by a health care provider. Examples of such parameters include, by way of non-limiting example, third periods being delivered for between about 5 cycles and about 50,000 cycles, or third periods having durations lasting between about 1 minute and about 100 hours. Other ranges and values of cycles and third period durations are of course contemplated.

The various embodiments include two forms of stimulation. One such form of electrical stimulation is an on-off cycle of electrical stimulation embodiment, and the other such form of electrical stimulation is an increasing-decreasing electrical frequency, amplitude, intensity, and/or duration electrical stimulation embodiment, either which may be configured to produce high amplitude oscillations and/or resonance in the CVS of a patient.

In one embodiment, a third period created by interposed first and second periods may range between about 8 seconds and about 14 seconds, where the electrical stimulation is on for the first period and not on or off for the second period, where the signal of the first and second periods of time are together configured to create the third period which in turn triggers or induces resonance or high amplitude oscillations in a cardiovascular system of the patient. The first and second periods can be active or inactive for any period of time within the third period or total cycle. For example, if the third period is a 10 second cycle, the first on period can be where electrical stimulation is "on" for 5 seconds and the second "off" period can be for 5 seconds. The first period can range from between about 4 seconds and about 7 seconds, and the second period of time can range between about 4 seconds and about 7 seconds, creating a total cycle or third period of between about 8 seconds and about 14 seconds. Such a cycle of stimulation can be repeated to cause high amplitude oscillations and or resonance in the CVS of a patient.

In another embodiment, a third period created by interposed first and second periods may range between about 8 seconds and about 14 seconds, where in the electrical stimulation is increasing in electrical frequency, intensity, and/or pulse width during the first period and decreasing in electrical frequency, intensity, and/or pulse width during the second period, where the signals within the first and second periods of time are together configured to create the third period to trigger or induce resonance or high amplitude oscillations in a cardiovascular system of the patient. For example, if the third period is a 10 second cycle, the first increasing period can be for 5 seconds and the second decreasing period can be for 5 seconds. This cycle of stimulation can be repeated to cause high amplitude oscillations and or resonance in the CVS of a patient.

Combined methods, such as by way of non-limiting example, providing a stable, relatively uniform or unchanging electrical stimulation regime during a first period, and an increasing or "off" electrical stimulation regime during a second period, are also contemplated, where the third period ranges between about 8 seconds and about 14 seconds. In one embodiment, the third period can be generated by assessing or determining a patient's resonance frequency by monitoring and analyzing or estimating a patient's heart rate, heart rate variability, respiratory rate, sinus arrhythmia rate, or other physiological criteria associated with a patient.

Figure 2:
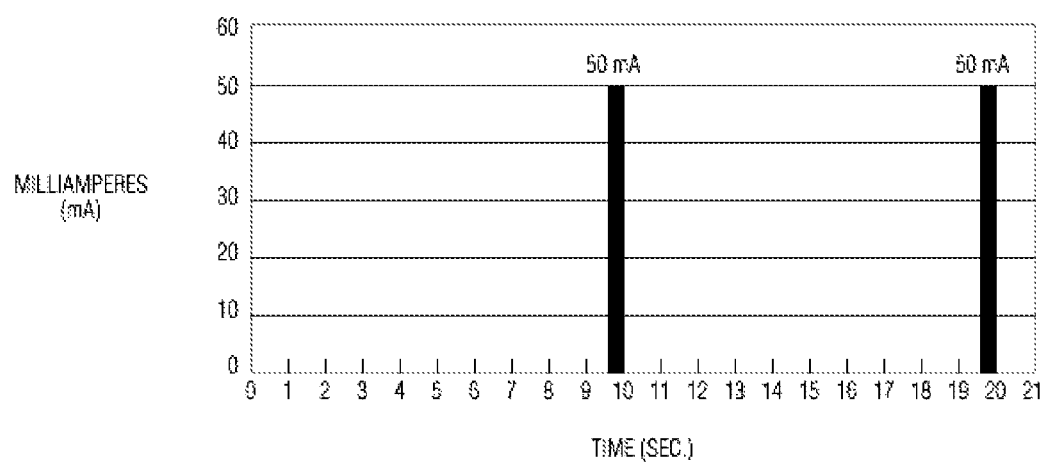
Figure 3:
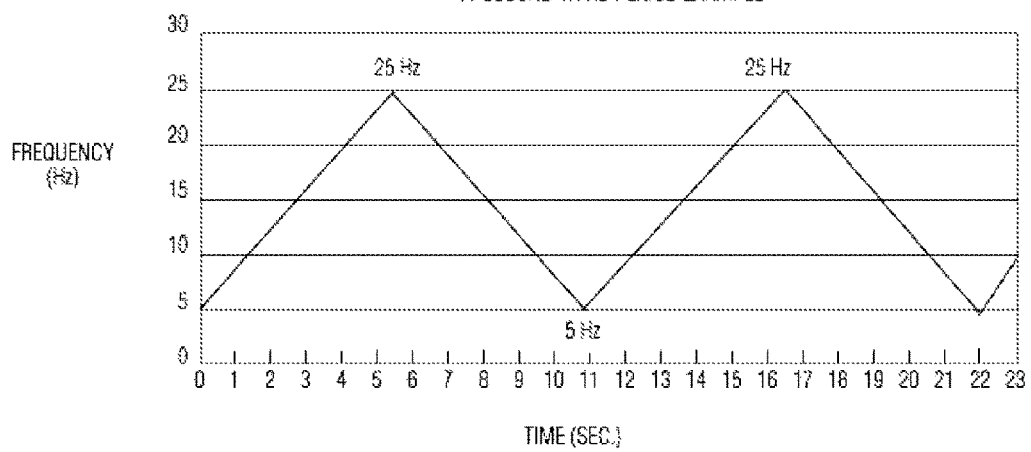

Various embodiments can comprise manipulating an electrical stimulation regime using the on-off and increasing-decreasing patterns described above using any suitable form of non-invasive or external electrical stimulation. One or more of the electrical stimulation's current, voltage, pulse width, frequency, amplitude or intensity, phase and duration can be modulated, modified, adjusted or optimized to provide the desired therapy. For example, electrical stimulation may be provided that ranges between about 0 mA and about 1 mA, between about 1 mA and about 5 mA, between about 1 mA and about 30 mA, and between about 1 mA and about 300 mA. Many different electrical stimulation parameters are contemplated, including those where stimulation signal voltage, pulse width, frequency, amplitude, intensity, phase, and duration are modulated or adjusted. FIGS. 1 through 3 illustrate various illustrative but non-limiting embodiments of external electrical stimulation regimes and corresponding methods that can be provided to a patient.

Figure 4:
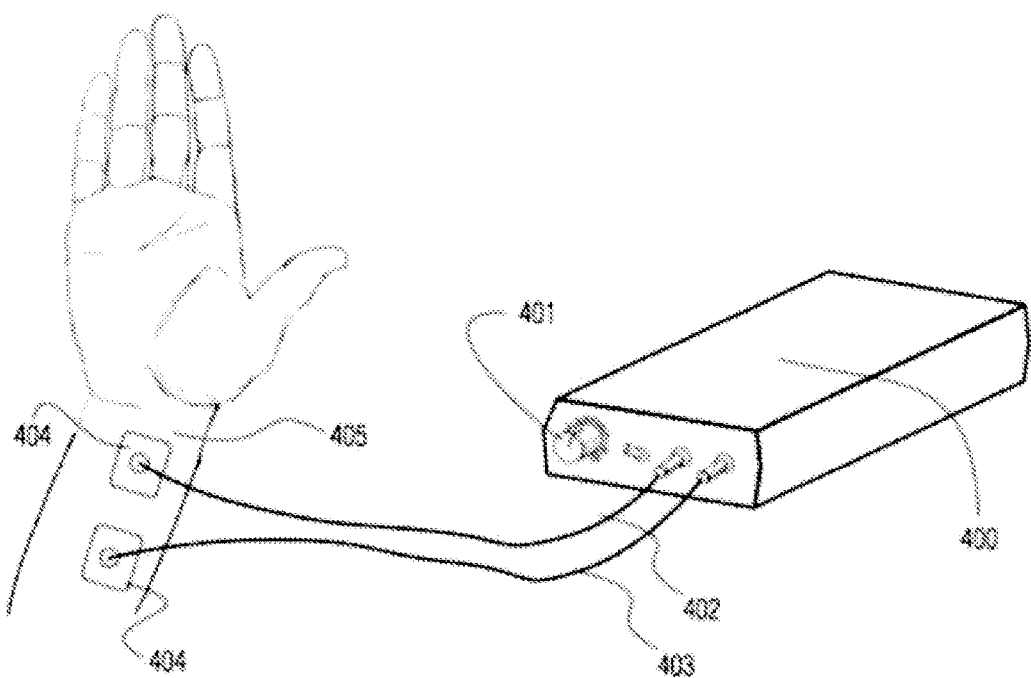
FIGS. 4 through 5 illustrate various embodiments of wearable or portable systems and/or components thereof.
Figure 5:
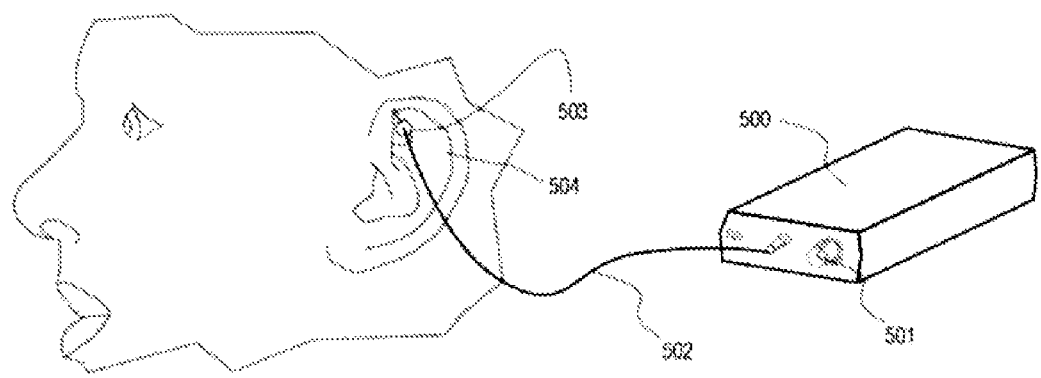

Referring now to FIGS. 4 and 5, and using a transcutaneous electrical nerve stimulation (TENS) device as an example, we show how one embodiment may be employed to provide therapy to a patient. A TENS unit is used to supply low voltage electrical currents that are passed through a patient's skin to the underlying nerves via surface electrodes. The TENS unit has an electrical generator for generation of current signals that can be manipulated to alter the electrical frequency, the pulse duration, the pulse intensity, and potentially other electrical stimulation parameters. The pulse width on a TENS device may range, by way of non-limiting example, between about 1 µS and about 250 µS, have an intensity or amplitude that ranges between about 0 mA and about 100 mA, or between about 5 mV and about 100 mV, and/or have a frequency that ranges between about 1 Hz and about 250 Hz, or between about 10 Hz and bout 50 Hz.

In one embodiment, and as shown in FIG. 1, electrical stimulation is provided to a patient using some of the electrical stimulation parameters described above. For example, electrical stimulation signals having a pulse width of about 50 µS, an amplitude of about 10 mA, a frequency of about 40 Hz, or a voltage of about 100 mV can be delivered for 6 seconds, followed by an "off" or no electrical stimulation regime of about 6 seconds, which create a 12 second total cycle (or third period) of on-off electrical stimulation, where the second period of time follows the first period of time to create a total cycle or third period of 12 seconds (see FIG. 1). Variations in any one or more of electrical stimulation pulse width, frequency, amplitude, voltage, first period duration, second period duration, the duration of the third cycle, the duration of the "on" period, and the duration of the "off period" are contemplated.

In another embodiment, electrical stimulation is initiated at with a pulse width of about 1 µS, an amplitude of about 10 mA, and/or a frequency of about 40 Hz, and then increased to about 5 µS, about 15 mA, or about 60 Hz over a duration of a first 5 second period of time, followed by slowly decreasing such values over a second 5 second period of time back to the initial stimulation values, thereby creating a 10 second cycle of increasing and decreasing electrical stimulation, where the second period of time follows the first period of time to create a total cycle or third period of 10 seconds. Variations in any one or more of electrical stimulation pulse width, frequency, amplitude, voltage, first period duration, second period duration, the duration of the third cycle, the duration of the "on" period, and the duration of the "off period" are contemplated. Thus, frequency can increase from 10 Hz to 100 Hz while intensity and width remain constant over the cycle, while another embodiment may include rising and falling signal amplitudes and intensities while other parameters remain constant over the cycle, and so on.

Changes in electrical stimulation can be achieved via any method that can manipulate the voltage, current, frequency, amplitude, pulse width, and/or duration of the electrical stimulation to create the repeating cycles of the first, second and third periods as described above, with the primary third period cycles causing high amplitude oscillations and or resonance in the CVS of a patient. However, since one patient's resonance frequency can be different from that of another patient, different stimulation cycles are contemplated for different individuals within the 8 to 14 second third periods described herein.

Different embodiments can be employed in different types of devices to deliver the electrical stimulation (e.g., watches, medical devices). For example, transcranial direct current stimulation (tDCS) is a noninvasive, painless brain stimulation treatment in which direct electrical current or DC is used to stimulate particular parts of the brain. In this method, a low voltage direct current is fed constantly to a specific portion of the brain with the help of external electrodes. Typically tDCS therapy is delivered over periods of time ranging between 10 and 30 minutes, but may also be delivered continuously, for example, 0.2 mA and 1000 Hz over the entire period. In one embodiment, electrical stimulation is on or increasing during a first period of time, and off or decreasing during a second period of time to create a total cycle or third period. There are generally two types of electrical stimulation employed in tDCS: anodal stimulation and cathodal stimulation. Anodal stimulation acts to excite neuronal activity while cathodal stimulation inhibits or reduces neuronal activity. In one embodiment, high amplitude oscillations in the CVS are induced or generated at specific frequencies which can enhance the effectiveness of tDCS-based therapy for various psychiatric disorders such as depression, anxiety, attention problems, and schizophrenia.

In another embodiment, therapy is provided using neuromuscular electrical stimulation (NMES) or electrical muscle stimulation (EMS), which is the evocation of muscle contraction with the help of electrical stimulation. Electrical stimulation is employed to mimic the action potentials induced by the central nervous system, causing the muscles to contract. When using progressive muscle relaxation involves tensing muscles and relaxing muscles at specific frequencies, resonance or high amplitude oscillations can be induced in the CVS of a patient. Automatic passive stimulation through NMES or EMS can be provided by means of suitable electrical stimulation. NMES or EMS metrics of electrical stimulation can include manipulations of pulse shape (e.g., both monophasic and biphasic pulses), pulse width, amplitude or intensity of the electrical stimulation, and the frequency of the electrical stimulation. Various embodiments include NMES or EMS electrical stimulation regimes, and the provision of on-off or ramping up/ramping down electrical stimulation signals to cause or induce high amplitude oscillations or resonance in the CVS of a patient.

In another embodiment, magnetic field frequencies are modulated or adjusted to provide an electromagnetic therapy which applies electromagnetic radiation or pulsed electromagnetic fields (PEMF) to the body or brain (e.g., transcranial magnetic stimulation). In such embodiments, changes in electrical current, voltage or other signal parameters alter magnetic fields and forces using the techniques described above.

One embodiment includes identifying a patient's resonance frequency through EKG, HRV-HR monitor, HRV-HR watch, HRV-HR video capture, radar, or Doppler means, and to then automatically or manually trigger a pattern of electrical stimulation to induce resonance for the patient. Another embodiment employs other metrics such as galvanic skin response to measure sympathetic activity or muscle tension to trigger appropriate electrical stimulation. Other sensed physiological parameters are also contemplated to trigger electrical stimulation. In yet another embodiment, automated stimulation cycles having 11 second third periods are employed to trigger oscillations close to a patient's resonance frequency.

Electrical stimulation can be provided anywhere on the human body, including the ear (see FIG. 5). The neck and arm are preferred due to their ability to transmit signals to manipulate or modulate the CVS, as well as for comfort reasons. As noted above, such electrical stimulation signals can be provided by electrical stimulation devices such as an ALPHSTIM device manufactured by Electromedical Products International, Inc., where a third cycle is programmed to include on-off and/or increasing-decreasing cycles.

Referring now to FIG. 4, there is shown one embodiment of a device for delivering electrical stimulation to a patient, where TENS unit 400 includes an electrical current selector 401 and two electrically conductive electrodes 402 and 403 which are connected to adhesive pads 404 pressed to the skin 405. TENS unit 400 is configured to deliver on-off and/or increasing-decreasing electrical stimulation signals as described above.

In FIG. 5, there is shown another embodiment of a device for delivering electrical stimulation to a patient, wherein TENS unit 500 consists of an electrical current selector 501 and an electrically conductive electrode 502 that connects to a single ear clip 503 pressed into the concha of the ear 504. TENS unit 500 is configured to deliver on-off and/or increasing-decreasing electrical stimulation signals as described above.

The above described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

The resonance or high amplitude oscillations induced or created by the methods described and disclosed herein may be used to treat a patient for a stress-related disorder, depression, hypertension, an autonomic dysfunction, atrial fibrillation, coronary heart disease, diabetes, post-traumatic stress disorder, substance abuse, and yet other disorders, maladies or diseases. Such induced or created resonance, or forced oscillations, can also be employed to increase a patient's baroreflexes, increase the flexibility of a patient's CVS, and/or increase or improve a patient's vagal nerve tone and/or stress reactivity.

Successive cycles comprising the illustrated first and second periods may then be repeated as long as desired to effect suitable entrainment of the CVS. Successive cycles can also be terminated, adjusted or modified in accordance with physiological parameters of the patient that have been sensed, more about which is said below.

We claim:

1. A method of providing external electrical stimulation therapy to a patient, comprising:
   determining a resonance frequency of a cardiovascular system associated with the patient;
   determining parameters for at least one electrical stimulation signal based on the resonance frequency of the cardiovascular system associated with the patient, wherein the parameters include a first time period associated with a first type of electrical stimulation signal and a second time period associated with a second type of electrical stimulation signal and wherein a third period that is equivalent to a combination of the first time period and the second time period and that is also equivalent to the resonance frequency of the cardiovascular system of the patient; and
   electrically inducing the resonance frequency in the cardiovascular system associated with the patient by repetitively delivering at least one electrical stimulation signal having the determined parameters to at least one location on the patient's skin or a layer disposed next to the patient's skin;
   wherein the electrical stimulation signal includes (i) the first type of the electrical stimulation signal being successively delivered to the patient over the first time period and (ii) the second type of the electrical stimulation signal being delivered to the patient over the second time period, the second time period being interposed between instances of the first time period.

2. The method of claim 1, wherein the first time period is adjacent to the second time period.

3. The method of claim 1, wherein the individual's heart rate (HR) resonant frequency is employed to determine the third time period.

4. The method of claim 1, wherein the third time period ranges between about 8 seconds and about 14 seconds.

5. The method of claim 1, wherein the first time period ranges between about 4 seconds and about 7 seconds.

6. The method of claim 1, wherein the second time period ranges between about 4 seconds and about 7 seconds.

7. The method of claim 1, wherein the electrical current of the first type of the electrical stimulation signal provided during the first time period is substantially uniform.

8. The method of claim 1, wherein the frequency of the first type of the electrical stimulation signal provided during the first time period is substantially uniform.

9. The method of claim 1, wherein the pulse width of the first type of the electrical stimulation signal provided during the first time period is substantially uniform.

10. The method of claim 1, wherein the first periods of time correspond to an "on" mode while the first type of the electrical stimulation signal is being delivered to the patient, and the second periods of time correspond to an "off" mode while the second type of the electrical stimulation signal is being delivered to the patient.

11. The method of claim 1, wherein the first time period corresponds to an "increasing" mode while the first type of the electrical stimulation signal is being delivered at increasing frequency, amplitude or pulse width to the patient, and the second time period corresponds to a "decreasing" mode while the second type of the electrical stimulation signal is decreasing in frequency, amplitude or pulse width.

12. The method of claim 1, further comprising sensing a physiological parameter of the patient and, in response to such sensing, adjusting the third period.

13. The method of claim 1, further comprising sensing a physiological parameter of the patient and, in response to such sensing, changing the lengths of at least one of the first time period and the second time period.

14. The method of claim 1, further comprising sensing a physiological parameter of the patient and, in response to such sensing, initiating delivery of the first type or the second type of the electrical stimulation signal to the patient.

15. The method of claim 1, further comprising sensing a physiological parameter of the patient and, in response to such sensing, terminating delivery of the first type or the second type of the electrical stimulation signal to the patient.

16. The method of claim 1, wherein the induced resonance or high amplitude oscillations aid in treating the patient for a stress-related disorder, depression, hypertension, autonomic dysfunction, atrial fibrillation, coronary heart disease, diabetes, or other cardiovascular disease.

17. The method of claim 1, wherein the external electrical stimulation therapy is provided to the patient for a period of time ranging between about 60 seconds and 24 hours.

* * * * *